United States Patent [19]

Akabane et al.

[11] Patent Number: 4,931,562

[45] Date of Patent: Jun. 5, 1990

[54] PIPERIDINES

[75] Inventors: Yasuhiro Akabane, Chiba; Takamitsu Tamura, Tanashi; Masami Fujiwara, Tokyo, all of Japan

[73] Assignees: Lion Corporation, Tokyo, Japan; Sankyo Company Limited, Tokyo, Japan

[21] Appl. No.: 295,670

[22] Filed: Jan. 11, 1989

Related U.S. Application Data

[62] Division of Ser. No. 92,884, Sep. 4, 1987, Pat. No. 4,820,437.

[30] Foreign Application Priority Data

| | | | |
|---|---|---|---|
| Sep. 18, 1986 | [JP] | Japan | 61-220214 |
| Dec. 26, 1986 | [JP] | Japan | 61-315200 |
| May 28, 1987 | [JP] | Japan | 62-132698 |

[51] Int. Cl.[5] .................. C07D 471/10; C07D 211/46; C07D 211/58

[52] U.S. Cl. ...................................... 546/19; 546/223; 546/242; 546/246; 252/102

[58] Field of Search .................. 546/19, 223, 242, 244

[56] References Cited

PUBLICATIONS

"A Method of Detecting $O_2^-$ Production," Inorganica Chimica Acta, 24 (1977) L71–L73.

*Primary Examiner*—Robert T. Bond
*Attorney, Agent, or Firm*—Burns, Doane, Swecker & Mathis

[57] ABSTRACT

A bleaching composition comprises:

(A) hydrogen peroxide and/or a hydrogen peroxide addition compound such as a percarbonate; and (B) at least one activator which is a nitrogen-containing heterocyclic compound in which a halogen atom is substituted for the hydrogen atom of the secondary amino group or a non-heterocyclic N-halo-hindered amine compound, the hydrolysis constant of the activator being within the range of $1\times10^{-10}$ to $5\times10^{-6}$ (at 25° C.). Examples of the activator include 1-chloro-piperidine, 1-chloro-2-methyl-piperidine, 1-chloro-isonipecotic acid, 1-chloro- -hexamethyleneimine and 1-chloro-ε-caprolactam. The bleaching-detergent composition may also contain the components (A) and (B) together with a surfactant. These compositions exhibit an excellent effect concerning bleaching at low temperature, but hardly affect the colors of colored and patterned clothes.

2 Claims, No Drawings

PIPERIDINES

This application is a divisional of application Ser. No. 092,884, filed Sep. 4, 1987.

BACKGROUND OF THE INVENTION

1. Field of the Invention

The present invention relates to a bleaching composition and a bleaching detergent composition which are suitable for bleaching fibers and clothes, particularly for washing and bleaching fibrous products.

2. Prior Art

Various compounds such as hypochloride, bleaching powder, hydrogen peroxide, hydrogen peroxide addition compounds such as sodium percarbonate, persulfates, isocyanuric hydrochloride, and organic peroxides have been conventionally used as bleaching agents. Of these compounds, hydrogen peroxide and hydrogen peroxide addition compounds hardly affect the colors of colored and patterned clothes and are thus used as bleaching agents for clothes, namely they are widely used for bleaching out stains and black spots caused by tea, fruit juice, or cosmetics. However, such compounds have a problem in that their bleaching effects are generally low at low temperatures.

In order to solve the above-described problem, various different methods have been proposed in which various activators are added to bleaching agents to achieve effective bleaching at low temperatures.

Examples of such methods include a method in which a complex comprising EDTA and a heavy metal such as iron, manganese, or cobalt is used as an activator to promote the decomposition of hydrogen peroxide (U.S. Pat. No. 315664) and a method in which a compound which produces peracetic acid when reacted with hydrogen peroxide in a bleaching bath, i.e., carboxylic acid anhydride (U.S. Pat. No. 2362401) or an N-acylated compound (Japanese Patent Publication No. 10165/1963) is used. However, the method using a heavy metal complex has a low activation efficiency and cannot provide a sufficient effect concerning bleaching at low temperatures. In addition, the method employing the addition of a peracetic acid-producing compound exhibits a high activation efficiency, but has disadvantages in that, when stains such as tea or fruit juice stains are removed, the oxidative effect of the active oxygen species contained in the bath is too high and thus the dye coloring matters present on colored and patterned clothes are simultaneously oxidized, resulting in changes in color.

On the other hand, it is known that Sodium N-chlorotoluene-P-sulphonamide, which is a N-halosulfonamide derivative, is used for the desizing and the bleaching purification of fibers (Japanese Patent Un-Examined Publication No. 110979/1969). In addition, a method has been proposed in which a halogen ion-producing compound, such as hypochlorite or a halogenated isocyanurate added to detergents is stabilized by using a sulfonamide derivative (Japanese Patent Un-Examined Publication No. 14299/1986). However, if these techniques are used, it is impossible to obtain a bleaching agent which exhibits an excellent effect of bleaching at low temperatures but which does not affect the colors of colored and patterned clothes.

SUMMARY OF THE INVENTION

It is, therefore, a primary object of the present invention to provide a bleaching composition which exhibits an excellent effect concerning bleaching at low temperatures but which hardly affects the colors of colored and patterned clothes. This and other objects of the present invention will be clear from the following description.

Hydroxyl radicals (·OH) and singlet oxygen ($^1O_2$) are known as active oxygen species which are released from peroxide compounds and exhibit bleaching effects. The present inventors have found that, of these species, ·OH has problems from the user's point of view in that it has a very high oxidative effect and exhibits a high bleaching effect on both the coloring matters of stains and also dyes, resulting in changes in the colors of colored and patterned clothes. On the other hand, it has also been found that $^1O_2$ exhibits a mild oxidative effect as compared with OH and a low bleaching effect on dye coloring matters, but has a sufficiently high bleaching effect on the coloring matters as stains. As a result of investigations on the basis of the above-described findings, it has been found that when hydrogen peroxide or an addition product thereof is combined with a specific activator, singlet oxygen is efficiently produced, and this finding has led to the achievement of the present invention.

In accordance with the present invention, there is provided a bleaching composition comprising:

(A) hydrogen peroxide and/or a hydrogen peroxide addition compound; and (B) at least one activator which is a nitrogen-containing heterocyclic compound in which a halogen atom is substituted for the hydrogen atom of the secondary amino group or a non-heterocyclic N-halo-hindered amine compound, the hydrolysis constant of the activator being within the range of $1\times10^{-6}$ to $5\times10^{-6}$ (at 25° C.); and provided a bleaching detergent composition containing the composition described above.

DESCRIPTION OF THE PREFERRED EMBODIMENTS

The hydrogen peroxide addition compound of component (A) is a compound which releases hydrogen peroxide in a water bath. Examples of such compounds include percarbonates, perborates, perphosphates, and hydrogen peroxide addition compounds of urea. Examples of such salts include sodium salts, potassium salts, lithium salts, and calcium salts. Among these compounds, sodium percarbonate or sodium perborate is preferably used.

The present invention is characterized by the combination of one of the above-described hydrogen peroxide addition products of a mixture of two or more addition products and/or hydrogen peroxide, with an activator as component (B) which is a nitrogen-containing heterocyclic compound in which a halogen atom is substituted for the hydrogen atom of the secondary amino group in the heterocycle and which has a hydrolysis constant of $1\times10^{-10}$ to $5\times10^{-6}$ (at 25° C.). A preferable compound used as the nitrogen-containing heterocyclic compound (B-1) of component (B) in which a halogen atom is substituted for the hydrogen atom of the secondary amino group in the heterocycle is a 1-halopiperidine derivative having the following Formula (I):

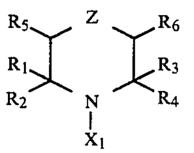

[I]

(wherein $R_1$ to $R_6$ each denotes a hydrogen or alkyl group and may be the same as or different from each other. $R_1$ and $R_2$ or $R_3$ and $R_4$ may be bonded to each other to form the following cycles involving the carbon atoms to which they are bonded:

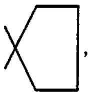, 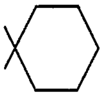 or 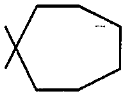

$X_1$ denotes a halogen atom and Z denotes a group having the following formula:

$—CH_2—$, 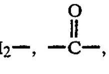, 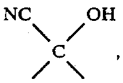, 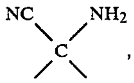,

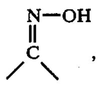, 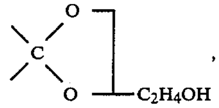,

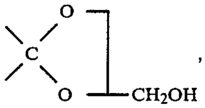, or 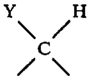

wherein Y denotes an alkoxyl, hydroxyl, or carboxyl group, —NCS, $—CONH_2$,

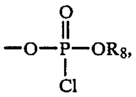, —O-sugar residue, 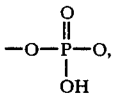,

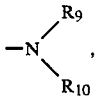, or 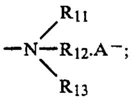;

$R_8$ is an alkyl having 1 to 16 carbon atoms, phenyl; $R_9$ and $R_{10}$ may be the same or different and each denotes $C_mH_{2m+1}$, $C_mH_{2m}OH$, $C_mH_{2m-1}(OH)_2$, $C_mH_{2m}COOM_1$ (wherein $M_1$ denotes H or an alkali metal), or an alkanoly group; $R_{11}$ and $R_{12}$ may be the same or different and each denotes $C_mH_{2m+1}$, $C_mH_{2m}OH$ or $C_mH_{2m}$; $R_{13}$ denotes a hydrogen atom or $C_mH_{2m+1}$; m is an integer from 1 to 4; and $A^-$ denotes an anionic residue, for example $Cl^{-1}$, $CH_3COO^-$, or

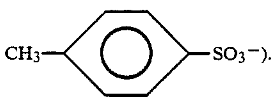).

It is preferable to use a 1-halopiperidine derivative of a hindered type having Formula (I) wherein $R_1$ to $R_4$ each denotes an alkyl group, $R_5$ and $R_6$ each denotes a hydrogen atom, and Z denotes a group having:

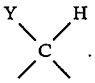.

It is particularly preferable to use a 1-halopiperidine derivative of hindered type having Formula (I) wherein $R_1$ to $R_4$ each denotes a methyl group, $R_5$ and $R_6$ each denotes a hydrogen atom, $X_1$ denotes a chlorine atom, Z denotes

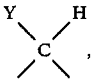,

Y denotes a hydroxyl group, a lower alkoxyl group,

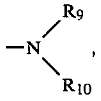, or 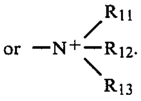.

Examples of the alkyl group in the above-described formula include groups having 1 to 12 carbon atoms, preferably 1 to 4 carbon atoms, more preferably a methyl group; and examples of the lower alkoxyl group include groups having 1 to 4 carbon atoms. Examples of the lower alkanoyl group include groups having 2 to 8 carbon atoms. An example of the sugar residue is

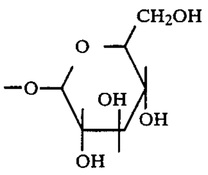

The compound having the above-described Formula (I) can be produced by, for example, the method described below.

An amine compound (>NH) used as a raw material is dissolved in an inactive solvent and, if required, solid carbonic acid is then added to the thus-obtained solution to produce the intended N-halogen compound (>N—X). There is no particular limit on the inactive solvent used unless it is related to the reaction, but preferable examples of this solvent include water, alcohols, and mixed solvents of halogenated hydrocarbons and water.

Examples of halogenating agents include alkali or alkali earth metal salts of hypohalogenous acids.

The reaction temperature is within the range of 0° C. to room temperature, and the time required for the reaction is within the range of 30 minutes to 5 hours.

After the reaction has been completed, the target compound can be collected from the reaction mixture by a conventional method. For example, the water-insoluble organic solvent can be extracted from the reaction mixture and the solvent can be removed by drying the obtained extract to obtain the target compound. If required, the obtained compound can then be purified by, for example, column chromatography, distillation, or recrystallization.

The ammonium salt of the target compound can be produced by dissolving the N-halogen compound obtained by the above-described method in an inactive solvent and reacting it with an acid or an ester thereof.

There is no particular limit with respect to the inactive solvent unless it relates to the reaction, but preferable examples of the solvent include alcohols such as methanol and ethanol. After the reaction has been completed, the target compound can be collected from the reaction mixture by a conventional method. For example, after the reaction has been completed, the target compound can be obtained by concentrating the solvent of the reaction mixture and, if required, it can then be purified by recrystallization.

Examples of the compound expressed by Formula (I) are given below.

(1-Chloro-piperidine derivatives)

1-Chloro-piperidine:

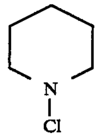

1-Chloro-2-methyl-piperidine:

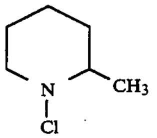

1-Chloro-3,5-dimethyl-piperidine:

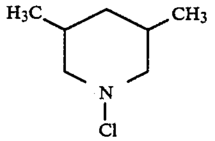

1-Chloro-isonipecotic acid:

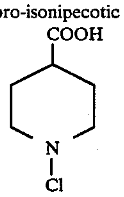

1-Chloro-2,2,6,6-tetramethyl-piperidine:

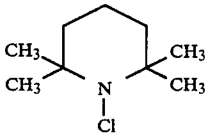

1-Chloro-2,2,6-trimethyl-6-isobutylpiperidine:

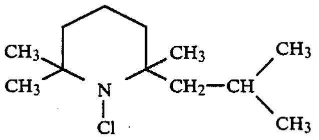

1-Chloro-4-oxo-2,2,6,6-tetramethylpiperidine:

-continued

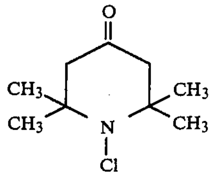

1-Chloro-4-oxo-2,2,6-trimethyl-6-n-hexylpiperidine:

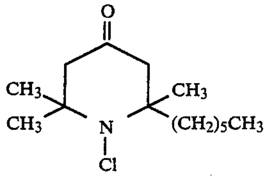

6-Chloro-6-aza-7,7-dimethyl-9-oxo-spiro[4.5]decane:

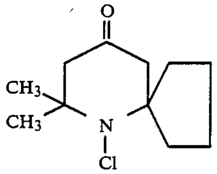

1-Chloro-1-aza-2,2-dimethyl-4-oxo-spiro[5.5]undecane:

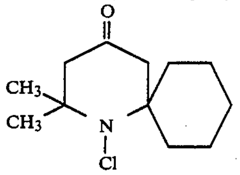

1-Chloro-4-hydroxy-2,2,6,6-tetramethylpiperidine:

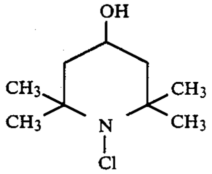

1-Chloro-4-hydroxyimino-2,2,6,6-tetramethylpiperidine:

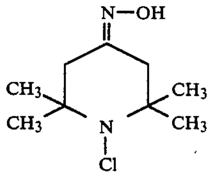

1-Chloro-1-aza-2,2-dimethyl-4-hydroxyimino-spiro[5.5]undecane:

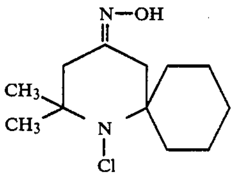

1-Chloro-4-hydroxy-4-cyano-2,2,6,6-tetramethylpiperidine:

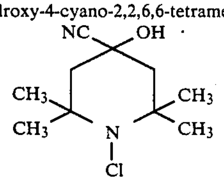

1-Chloro-1-aza-2,2-dimethyl-4-hydroxy-4-cyano-spiro[5.5] undecane:

-continued

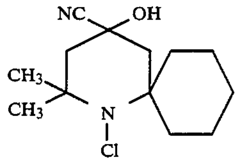

1-Chloro-4-amino-4-cyano-2,2,6,6-tetramethylpiperidine:

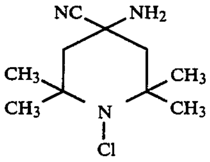

1-O-(1'-chloro-2',2',6',6'-tetramethyl-4'-piperidyl)-glycoside:

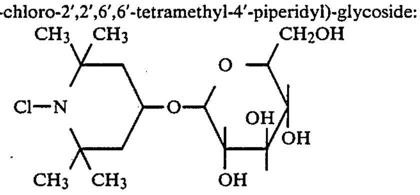

1-Chloro-2,2,6,6-tetramethyl-4-piperidylphosphate:

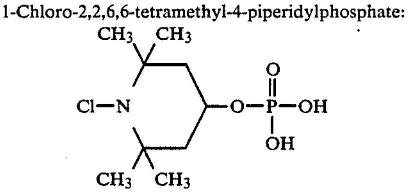

1-Chloro-2,2,6,6-tetramethyl-4-isothiocyanatopiperidine:

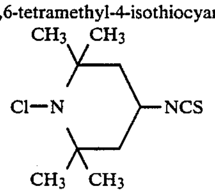

1-Chloro-4-[N-(2-hydroxyethyl)methylamino]-2,2,6,6-tetramethylpiperidine:

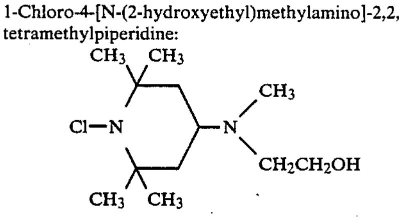

1-Chloro-4-[N-(2,3-dihydroxypropyl)methylamino]-2,2,6,6-tetramethylpiperidine:

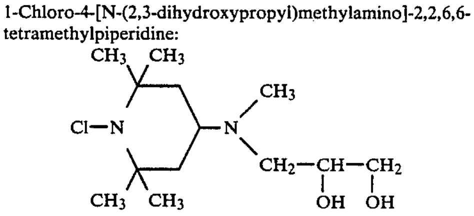

1-Chloro-4-[N-(2-hydroxyethyl)butylamino]-2,2,6,6-tetramethylpiperidine:

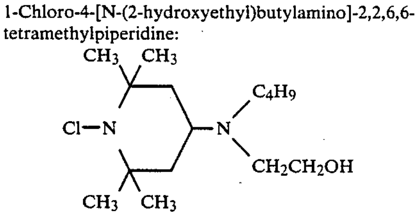

-continued

1-Chloro-4-[N-(2,3-dihydroxypropyl)butylamino]-2,2,6,6-tetramethylpiperidine:

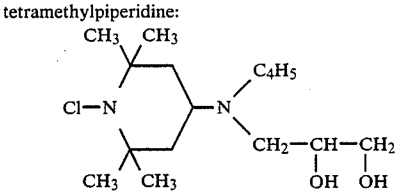

1-Chloro-4-[N,N-bis(2-hydroxyethyl)amino]-2,2,6,6-tetramethylpiperidine:

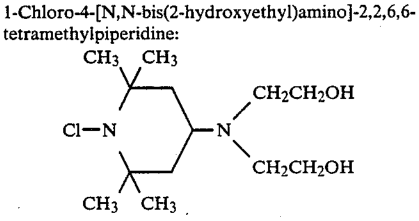

1-Chloro-4-[N-(2-hydroxyethyl-N-(2,3-dihydroxypropyl)amino]-2,2,6,6-tetramethylpiperidine:

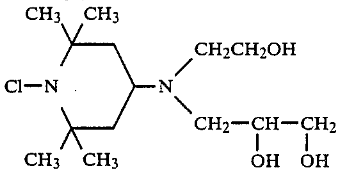

1-Chloro-4-[N-acetyl-N-methylamino]-2,2,6,6-tetramethylpiperidine:

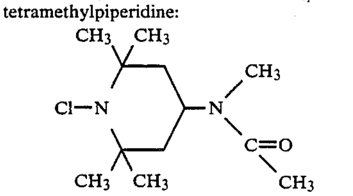

1-Chloro-4-[N-acetyl-N-butylamino]-2,2,6,6-tetramethylpiperidine:

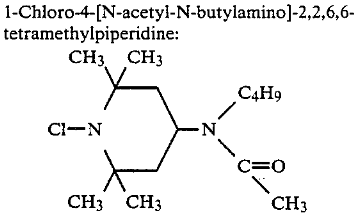

Trimethyl-(1-chloro-2,2,6,6-tetramethyl-4-piperidyl) ammonium paratoluenesulfonate:

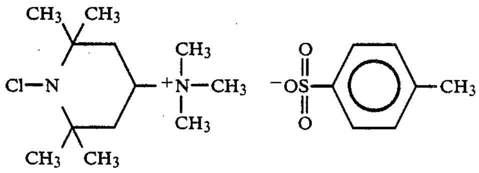

Dimethyl-(1-chloro-2,2,6,6-tetramethyl-4-piperidyl) ammonium chloride:

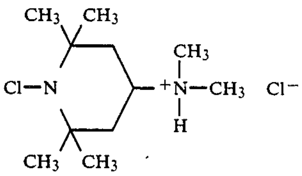

Dimethyl-(1-chloro-2,2,6,6-tetramethyl-4-piperidyl) ammonium acetate:

-continued

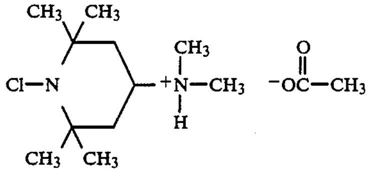

Methyl-(2-hydroxyethyl)-(1-chloro-2,2,6,6-tetramethyl-4-piperidyl) ammonium chloride:

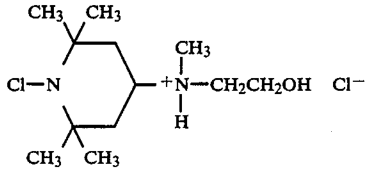

Di(2-hydroxyethyl)-(1-chloro-2,2,6,6-tetramethyl-4-piperidyl ammonium chloride:

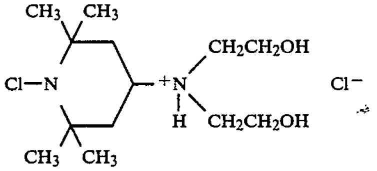

Dimethyl-benzyl-(1-chloro-2,2,6,6-tetramethyl-4-piperidyl) ammonium bromide:

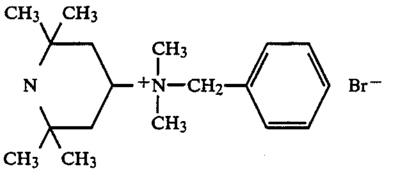

Spiro[4.4]-8-chloro-2-hydroxymethyl-7,7,9,9-tetramethyl-8-aza-1,4-dioxadecane:

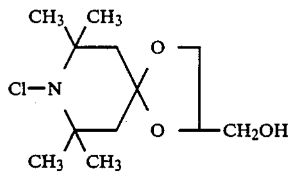

1-Chloro-4-methoxy-2,2,6,6-tetramethylpiperidine:

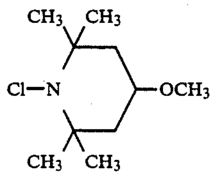

1-Chloro-4-[N,N-bis(sodium oxycarbonylmethyl)amino]-2,2,6,6-tetramethylpiperidine:

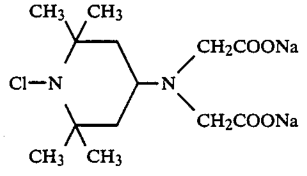

(Morpholine derivatives)

1-Chloro-morpholine:

-continued

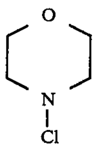

(Hexamethyleneimine derivatives)

1-Chloro-hexamethyleneimine:

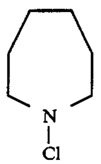

1-Chloro-ε-caprolactam:

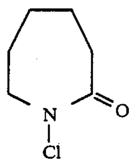

(Diazacycloheptanone derivatives)

1-Chloro-2,2,7,7-tetramethyl-1,4-diazacycloheptane-5-one:

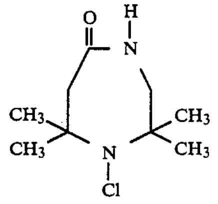

These compounds are used singly or as mixtures of two or more compounds. Among the above-described compounds, preferable compounds are 1-chloro-piperidine, 1-chloro-2-methylpiperidine, 1-chloro-3,5-dimethylpiperidine, 1-chloroisonipecotic acid, 1-chloromorpholine, 1-chloro-ε-caprolactam, 1-chloro-hexamethyleneimine, 1-chloro-4-,N-(2,3-dihydroxypropyl)-butylamino.-2,2,6,6-tetramethylpiperidine, 1-chloro-4-,N-N-bis(sodium oxycarbonylmethyl)amino.-2,2,6,6-tetramethylpiperidine, spiro,4.5.-8-chloro-2-hydroxymethyl-7,7,9,9-tetramethyl-8-aza-1,4-dioxadecane, 1-chloro-4-methoxy-2,2,6,6-tetramethylpiperidine, 1-chloro-4-hydroxy-2,2,6,6-tetramethylpiperidine, 1-chloro-4-,N-(2-hydroxypropyl)methylamino.-2,2,6,6-tetramethylpiperidine, 1-chloro-4-,N-(2,3-dihydroxypropyl)methylamino.-2,2,6,6-tetramethylpiperidine, 1-chloro-4-,N,N-bis(2-hydroxyethyl)amino.-2,2,6,6-tetramethylpiperidine, and trimethyl-(1-chloro-2,2,6,6-tetramethyl-4-piperidyl) ammonium paratoluenesulfonate. Among these compounds, particularly preferable compounds are 1-chloro-hexamethyleneimine, 1-chloro-4-hydroxy-2,2,6,6-tetramethylpiperidine, 1-chloro-,N-(2-hydroxyethyl)methylamino.-2,2,6,6-tetramethylpiperidine, 1-chloro-4-,N-(2,3-dihydroxypropyl)-methylamino.-2,2,6,6-tetramethylpiperidine, 1-chloro-4-,N,N-bis(2-hydroxyethyl)amino.-2,2,6,6-tetramethylpiperidine, and trimethyl-(1-chloro-2,2,6,6-tetramethyl-4-piperidyl) ammonium paratoluenesulfonate.

In addition, the N-halo-hindered amine compound (B-2) as the component (B) is the hindered amine compound having the following Formula (II) or (III) in which at least one halogen atom is substituted for the hydrogen atom of the amino group:

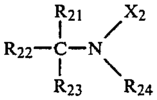
[II]

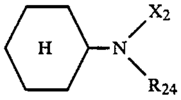
[III]

(wherein $R_{21}$, $R_{22}$, and $R_{23}$ each denotes —COOH, $—C_nH_{2n+1}$, $—C—(C_nH_{2n+1})_3$, $—C_nH_{2n}OH$, $—CH_2—C—(C_nH_{2n+1})_3$, $—C_nH_{2n}COOH$, $—OC_nH_{2n+1}$, or $—COOR_{25}$ (wherein $R_{25}$ denotes an alkyl group having 1 to 9 carbon atoms); $R_{24}$ denotes —H, —OH, —F, —Cl, —Br, —I, $—C_nH_{2n+1}$, $—C—(C_nH_{2n+1})_3$, $—C_nH_{2n}OH$, $—CH_2$, $—C—(C_nH_{2n+1})_3$, $—C_nH_{2n-1}(OH)_2$, $—(C_2H_4O)_nH$, $—C_nH_{2n}COOH$, $—C_nH_{2n}COOR_{26}$ (wherein $R_{26}$ denotes an alkyl group having 1 to 9 carbon atoms), $—C_nH_{2n}—SO_3M_2$, $—C_nH_{2n}OSO_3M_2$, $C_nH_{2n}PO_3$,H, or $—C_nH_{2n}CB$; n is an integer from 1 to 9; $M_2$, H or an alkali metal; and $X_2$, a halogen atom).

Examples of the compound (B-2) having the above-described formula include the following N-halo-t-alkylamines and derivatives thereof.

N-Chloro-t-butylamine:

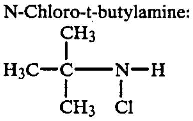

2-(N-Chloro-t-butylamino)-ethanol:

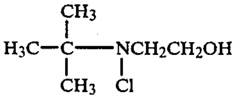

N-Chloro-1,1-dimethyl-propylamine:

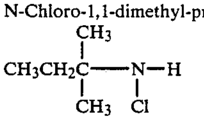

2-(N-Chloro-1,1-dimethyl-propylamino)-ethanol:

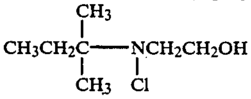

2-N-Chloroamino-2-methylpropanol:

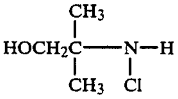

2-(N-Chloro-t-octylamino)-ethanol:

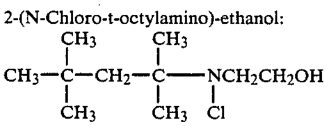

N-Chloro-t-octylamine:

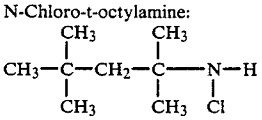

α-N-Chloroaminoisobutyric acid:

-continued

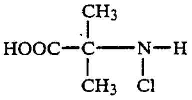

3-(N-Chloro-t-butylamino)-1-methyl-1,2-propanediol:

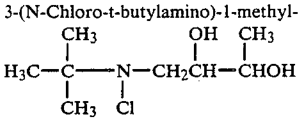

3-(N-Chloro-t-butylamino)-1,1-dimethyl-1,2-propanediol:

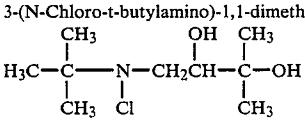

N-Chloro-t-butylaminoethane:

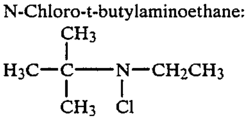

N-Chloro-di-t-butylamine:

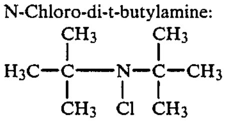

2-(N-Chloro-t-butylamino)-acetic acid:

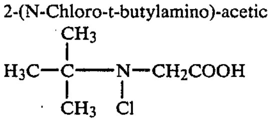

3-(N-Chloro-t-butylamino)-propionic acid:

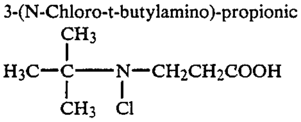

N-Chloro-t-butylaminomethanesulfonic acid:

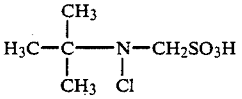

2-(N-Chloro-t-butylamino)-ethanesulfonic acid:

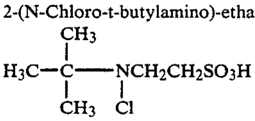

3-(N-Chloro-N-t-butylamino)-1,2-propanediol:

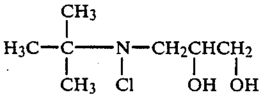

3-(N-Chloro-N-cyclohexylamino)-1,2-propanediol:

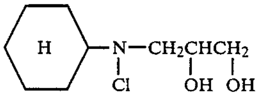

N-Chlorocyclohexylamine:

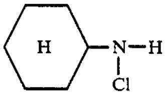

N-Chloro-N-methylcyclohexylamine:

-continued

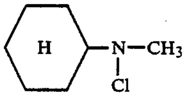

These compounds are used singly or as mixtures of two or more compounds. Among the above-described compounds, preferable compounds are N-chloro-t-butylamine, 2-(N-chloro-t-butylamino)-ethanol, 3-(N-chloro-t-butylamino)-1,2-propanediol, 2-(N-chloro-t-butylamino)-acetic acid, and 2-(N-chloro-t-butylamino)-methanesulfonic acid. The compounds (B-1) and (B-2) may be used in combination.

These compounds (B-1 and B-2) are characterized by each having the portion of a bulky chemical structure close to the H-halo-amino group, as shown in the above-described examples.

The amount of activator used as the component (B) is preferably 0.05 to 4.0 moles, more preferably 0.1 to 1.5 moles, relative to one mole of the hydrogen peroxide used or the hydrogen perodixe produced from the hydrogen peroxide addition product used.

It is conjectured that the excellent effects exhibited by the bleaching agent composition of the present invention are based on the following functional mechanism:

The activator of the present invention is hydrolyzed in water to release hypohalogenous acid ions ($OX^-$), as shown by the following equation:

$$N—X+H_2O \rightarrow N—H+OX^-+H^+ \quad (1)$$

$OX^-$ then reacts with hydrogen peroxide which is coexsistent in water to release $^1O_2$, as shown by the following Equation (2):

$$OX^-+H_2O_2 \rightarrow X^-+H_2O+{}^1O_2 \quad (2)$$

Since the $^1O_2$ released here has a lifetime as short as several micro seconds in water and is inactivated to ground-stage oxygen ($^3O_2$) which has limited bleaching activity, the reaction shown by Equation (2) must continuously take place to release $^1O_2$ at an appropriate speed in order to bleach stains in clothes during the time required for bleaching. Therefore, the hydrolysis constant (Kh) of an organic chlorine compound which is subjected to the hydrolysis shown by Equation (1) must be within the range of values that are not too large and the concentration of $OX^-$ in a bath must be maintained at appropriate value. For example, when a dichloroisocyanurate which is an organic chlorine compound having a high hydrolysis constant (Kh) is used, since the production speed of $^1O_2$ is too high, the released $^1O_2$ is most inactivated and thus fails to show a satisfactory bleaching effect.

In this manner, the reaction of an organic chlorine compound having an appropriate hydrolysis constant (Kh) with hydrogen peroxide can release at an appropriate speed $^1O_2$ which exhibits a high level of discoloration for the coloring elements of stains and a low degree of discoloration for dye coloring elements. The component (B) used in the present invention preferably has a hydrolysis constant (Kh) of $1.0\times10^{-10}$ to $5.0\times10^{-6}$ (at 25° C.), more preferably, $1.0\times10^{-8}$ to $1.0\times10^{-6}$ (at 25° C.).

The hydrolysis constant of the component (B) can be measured by, for example, the method described in J. Chem. Soc., 127, 98 (1925).

The principle of this method is described below.

When the precursor amine of a chloroamine having Kh to be measured is added to a solution of Dichloramine T having a known equilibrium constant of hydrolysis in a state of dissolution equilibrium, the chloroamine is produced in the solution so as to cause Dichloramine T to deviate from the dissolution equilibrium and to be maintained in a new equilibrium state. In this state, when the concentration of the chloride is titrated by an iodine color-producing method, the obtained concentration of the chlorides is as follows:

$$2a+b+x=T/2 \quad (3)$$

wherein a denotes the concentration of Dichloroamine T not hydrolyzed, b denotes the concentration of monochlorosulfonamide, x denotes the concentration of produced chloroamine, and T denotes the amount of sodium thiosulfate used for the the titration.

Therefore, the increment S of the titration value produced by the addition of the precursor amine is expressed by the following equation:

$$S=b+x=T/2-2a \quad (4)$$

The hydrolysis constants $K_1$, $K_2$ in the first and second steps of Dichloramine T are known, as described in J. Chem. Soc., 125, 1899 (1924).

$$K_1 = \frac{b \times h}{a} = 8.0 \times 10^{-7} \quad (5)$$

$$K_2 = \frac{c \times h}{b} = 4.9 \times 10^{-8} \quad (6)$$

wherein h denotes the concentration of HClO and c denotes the concentration of sulfonamide. From Equations (5) and (6), the following relation can be obtained:

$$K_1/K_2 = \frac{b_2}{ac} = 16.33 \quad (7)$$

On the other hand, a, which is the saturation solubility of Dichloramine T, can be measured:

$$a=0.97\times10^{-3}\ (M) \quad (8)$$

In addition, since x is equivalent to the concentration of HClO produced from Dichloramine T, $$x-b+2c \quad (9)$$

From Equations (4) to (9), $$b^2+15.84\times10^{-3}b-7.92\times10^{-3}S=0 \quad (10)$$

Since s can be measured and b, x, and h can be obtained from Equations (10), (4), and (5), respectively, the intended Kh of the chloroamine is expressed by the following Equation (11):

$$Kh = \frac{(d-x) \times h}{x} \quad (11)$$

wherein d can be obtained from the concentration of the precursor amine added.

It is preferable to use a solution in which the component (B) is dissolved in an amount of 0.01 g or more, more preferably 0.1 g or more, particularly preferably 1 g or more, relative to 100 g of a 0.01% aqueous solution of the component (A).

The bleaching composition of the present invention can be employed as it is or can be used as a bleaching agent in a mixture with conventionally-used components. In this case, the addition of 1 to 5% of a surfactant such as polyoxyethylene nonylphenyl ether (average oxyethylene chain length p=5 to 30) can advantageously promote the permeation of bleaching components into clothes in water and improve the effect of stain removal.

In addition, the bleaching composition of the present invention can be added as a bleaching effect-imparting component to granular detergent. In other words, the bleaching composition can be desirably used as a bleaching-detergent composition containing 0.1 to 0.3% by weight of the component (A), 0.1 to 30% by weight of the component (B), 0.1 to 50% of at least one surfactant selected from the group comprising anionic surfactants, nonionic surfactants, and ampholytic surfactants, as well as conventionally-used components such as zeolite, an alkali builder, a perfume, and a dyestuff.

Furthermore, when the bleaching composition of the present invention is added to an enzyme-containing detergent, the effect concerning the removal of stains such as proteins is obtained by the enzyme effect acting on an article to be washed, whereby an excellent bleaching effect can be obtained. Since alkali protease, which is widely used in the industry related to this invention, is known to be inactivated by active chlorine, it is difficult to say that the activator used in the present invention is preferable for an enzyme if it is used singly. However, it was found that a system of the present invention in which the activator is used in combination with hydrogen peroxide has only a slightly adverse influence upon an enzyme and shows an adequate bleaching effect.

Examples of the above-described anionic surfactants include linear alkyl benzenesulfonates in which the alkyl has 9 to 15 carbon atoms (C), alkylsulfates (particularly $C_{10}$ to $C_{22}$), olefin sulfonates (particularly $C_{10}$ to $C_{24}$), alkane and/or hydroxyalkane sulfonates (particularly $C_{10}$ to $C_{24}$), alkylphenoxy ether sulfate (particularly, having $C_8$ to $C_{12}$ alkyl groups and 1 to 10 ethylene oxide units), alkyl ether sulfates (particularly, having $C_{10}$ to $C_{20}$ alkyl groups and 1 to 10, preferably, 2 to 4, ethylene oxide units), and mixtures of one or more kinds of soap (particularly $C_{12}$ to $C_{20}$).

Examples of the nonionic surfactants include the condensation products of ethylene oxide and propylene oxide (typically 5 to 30 units) and aliphatic or aromatic alcohols or aliphatic amines or amides. Among these substances, aliphatic compounds preferably have $C_8$ to $C_{12}$ chains in the hydrophobic aliphatic portions thereof, and aromatic compounds preferably have alkyl aromatic groups having $C_6$ to $C_{12}$ chains.

Examples of the ampholitic surfactants include water-soluble derivatives of aliphatic quaternary ammonium, phosphonium, and sulfonium cationic compounds in each of which the aliphatic portion is a linear or branched chain, one substituent is $C_8$ to $C_{18}$, and an anionic water-soluble group, particularly a sulfonate group, is present at one end, such as alkyl-hydroxy-propane-sulfonates and alkyl-dimethyl-ammonium-hydroxy-propane-sulfonates.

Examples of the detergent builders include sodium sulfate, sodium carbonate, sodium silicate, sodium pyrophosphate, sodium tripolyphosphate, nitrilotriacetic acid and water-soluble salts thereof, sodium ethylenediaminetetraacetate, and various aluminosilicates such as Zeolite A. In this connection, it is preferable that the bleaching-detergent composition contains a builder in an amount of 5 to 90% by weight.

Typical examples of enzymes include protease such as alkalase produced by Novo Corp., esperase, and sabinase and alkali cellulase. In this regard, the bleaching-detergent composition may contain an enzyme in an amount of 0.01 to 10% by weight.

The bleaching operation comprises dissolving or dispersing the composition in water and immersing textile fabrics in the solution. The amount of bleaching agent used can be suitably selected according to the desired degree of bleaching. In addition, a temperature within the range of 20° to 40° C. is sufficient for bleaching, but one higher than 40° C. may of course be employed.

The present invention can obtain an excellent bleaching effect at a relatively low temperature and is extremely suitable for domestic washing because it produces not discoloration of colored and patterned clothes, as experienced when conventional activators are used. In addition, since the present invention is not only free from any tendency to cause discoloration of colored and patterned clothes but is also capable of bleaching textile fibers or pulp fibers while at the same time reducing embrittlement, it is suitable for bleaching industrial threads and fabrics and for bleaching in paper-making processes.

It is therefore obvious that the bleaching composition of the present invention can be widely used, and is also suitable for use as a bleaching agent for clothes. This bleaching composition is also useful as an additive for various detergents.

The present invention will now be described with reference to examples, though the present invention is not limited to these examples.

PRODUCTION EXAMPLES

Examples of the production of several preferred activators are used in the present invention is described below.

PRODUCTION EXAMPLE 1

1-Chloro-4-N,N-bis(2-hydroxyethyl)amino.-2,2,6,6-tetramethylpiperidine 3.82 g of 4-,N,N-bis(2-hydroxymethyl)amino.-2,2,6,6-tetramethylpiperidine was dissolved in a mixed solvent of 30 ml of dichloroethane and 10 ml of $H_2O$, and 1.85 g of calcium hypochlorite (bleaching powder) was gradually added to the obtained solution while agitating under ice cooling. 0.85 g of solid carbonic acid was then added to the mixture, followed by agitation at 0° C. for 15 minutes and then at room temperature for 1 hour. After completion of the reaction, the reaction mixture was subjected to extraction with dichloromethane, and an organic layer was then dried with sodium sulfate. The oily substance obtained by distilling off dichloromethane from the organic layer was subjected to silica gel column chromatography (eluent: ethyl acetate: triethylamine=30:1). The product was then recrystallized from a mixed solvent of hexane and ether (10:1) to obtain the target substance as crystals having a melting point of 54° to 56° C.

The corresponding amine compounds were subjected to the reactions described above, and the coarse products obtained were respectively purified by column chromatography and, if necessary, distillation and recrystallization, to obtain each of the intended substances described below.

1-Chloro-4-,N-(2-hydroxyethyl)-methylamino.-2,2,6,6-tetramethylpiperidine: mp, 37°-39° C.

1-Chloro-4-,N-(2,3-dihydroxypropyl)-methylamino.-2,2,6,6-tetramethylpiperidine: mp, 106°-107° C.

1-Chloro-4-,N-(2,3-dihydroxypropyl)-butylamino.-2,2,6,6-tetramethylpiperidine: TLC Rf=0.46 (silica gel, ethyl acetate: ethanol: triethylamine=20:1:1)

Spiro,4.5.-8-chloro-2-hydroxymethyl-7,7,9,9-tetramethyl-8-aza-1,4-dioxadecane: TLC Rf=0.34 (silica gel, ether: hexane=2:1)

1-Chloro-4-methoxy-2,2,6,6-tetramethylpiperidine: TLC Rf=0.42 (silica gel, hexane: ethyl acetate=10:1)

3-(N-Chloro-N-cyclohexylamino)-1,2-propanediol: mp, 55°-57° C.

3-(N-Chloro-N-t-butylamino)-1,2-propanediol: mp, 72°-73.5° C.

PRODUCTION EXAMPLE 2

1-Chloro-4-,N,N-bis(sodium oxycarbonylmethyl)amino.-2,2,6,6-tetramethylpiperidine 0.78 g of sodium hydroxide and 3.41 g of 1-chloro-4-N,N-bis(ethoxycarbonylmethyl)-.amino-2,2,6,6-tetramethylpiperidine which was obtained from 4-,N,N-bis(ethoxycarbonylmethyl)amino.-2,2,6,6-tetramethylpiperidine by the same method as that used in Production Example 1 were dissolved in 30 ml of ethanol, and the mixture was then agitated at room temperature for 15 hours. The produced insoluble substance was filtered off, washed with ethanol and then diethyl ether, and then dried under reduced pressure to obtain the intended substance as crystals showing the characteristic infrared absorption at 1598 $m^{-1}$ and 1428 $cm^{-1}$ (absorption of $-COO^{-}$).

PRODUCTION EXAMPLE 3

Trimethyl-(1-chloro-2,2,6,6-tetramethyl-4-piperidyl) ammonium paratoluenesulfonate 1.57 g of methyl paratoluenesulfonate and 1.79 g of 1-chloro-4-dimethylamino-2,2,6,6-tetramethylpiperidine which was obtained from 4-dimethylamino-2,2,6,6-tetramethylpiperidine by the same method as that of Production Example 1 were dissolved in 16 ml of methanol, and the mixture was then agitated at room temperature for 15 hours. After the reaction had completed, the crystals obtained by distilling off methanol from the reaction mixture were purified by recrystallization from a methanol-diethyl ether system to obtain the intended substance as crystals having a decomposition point of 202° to 204° C.

EXAMPLES

Description is now made of the method of forming stained cloth and dyed cloth and the method of measuring the bleaching effect and the degree of discoloration which were performed in Examples and Comparative Examples of the present invention.

Formation of Stained Cloth

Ten sheets of cotton broadcloth (pretreated cloth, 20×30 cm) purified by desizing were placed in a solution of the dyestuff extracted from 20 g of black tea with 1 l of water which was boiled for 5 minutes and then dyed while being boiled for 30 minutes. Each stained cloth was wrung, dried with air, and then cut into pieces each having a size of 5×5 cm which were then used in bleaching tests.

Formation of Dyed Cloth 0.75 g of a dye (C.I.No. Roactive Red-21) and 13.5 g of anhydrous sodium sulfate were dissolved in 450 ml of water and three sheets of cotton broadcloth (20×30 cm) purified by desizing were then placed in the obtained dye solution. The solution was maintained at 60° C. for 20 minutes and 9 g of sodium carbonate was then added to the solution, which was then maintained at 60° C. for 60 minutes. These sheets of cloth were then washed with water and then an aqueous 0.1% acetic acid solution, subjected to boiling treatment in an aqueous 0.2% anionic surfactant solution for 5 minutes, washed with water, dried, and then cut into pieces each having a size of 5×5 cm which were then used in discoloration tests.

Bleaching Test (i) Bleaching composition

Predetermined amounts of hydrogen peroxide or a hydrogen peroxide addition product and an activator were dissolved in 200 ml of water at 25° C. Five pieces of cloth stained with black tea were placed in this water bath and then subjected to bleaching treatment for 30 minutes. The cloths were then washed with water and dried to obtain bleached cloths. The degree of reflection of each pretreated cloth, black tea-stained cloth, and bleached cloth was measured by using a photoelectric reflection meter (ELREPHO produced by Carl Zeiss Co., Ltd.) and the bleaching ratio (%) thereof was obtained by the equation (12) described below.

(ii) Bleaching-detergent composition

A bleaching-detergent composition was added to water with a hardness of 3° DH at 25° C. so that the concentration became 0.8%, and a cloth stained with black tea was immersed in the water bath in a bath ratio of 50 times and then allowed to stand for 30 minutes. A clean cotton knitted cloth and water with a hardness of 3° DH at 25° C. were then added to the water bath and the bath ratio and the concentration of the detergent composition were adjusted to be 30 times and 0.15%, respectively, followed by washing a Terg-O-Tometer (produced by U.S. Testing Co., Ltd.) for 10 minutes at 120 rpm. The pieces of test cloth treated in the above-described manner were dehydrated for 1 minute, rinsed with overflowing water for 1 minute, and dehydrated for 1 minute in turn, and then dried by ironing to obtain bleached cloths.

The degree of reflection of each of the pretreated cloths, black tea-stained cloths, and bleached cloths was measured by using a photoelectric reflection meter (ELREPHO produced by Carl Zeiss Co., Ltd.) and the bleaching ratio thereof was obtained by the following equation (12):

Bleaching ratio (%) = (12)

-continued $$\frac{\text{Reflection degree of bleached cloth} - \text{reflection degree of black tea-stained cloth}}{\text{Reflection degree of pretreated cloth} - \text{reflection degree of black tea-stained cloth}} \times 100$$

In this test, when the bleaching ratio increased by 5%, an improvement in whiteness could be seen even by observation with the naked eye, and thus an improvement in the practical bleaching effect could be preceived.

Method of Measuring Discoloration

(i) Bleaching composition

A bleaching bath the same as that used in the bleaching test was prepared and two dyed pieces of cloth were then added into the bath, followed by bleaching treatment for 30 minutes. The cloths were then washed with water and dried with air, and the lightness and shade thereof were measured by using a differential colorimeter (DICOM ND504DE model produced by Nihon Denshoku-kogyo Co., Ltd.). The degree of discoloration E was obtained by the following equation (13):

$$E = \sqrt{\Delta L^2 + \Delta a^2 + \Delta b^2} \quad (13)$$

wherein $\Delta L$: change in lightness before and after the bleaching of the cloths.

$\Delta a$, $\Delta b$: change in shade before and after the bleaching of the cloths.

(A larger value of a means a redder color and a smaller value means a greener color. A larger value of b means a yellower color and a smaller value means a bluer color.)

In this test, when the degree of discoloration was 10 or more, the occurrence of discoloration could be noticed even by observation with the naked eye and thus a large discoloration was actually perceived.

(ii) Bleaching-detergent composition

A dyed piece of cloth was fixed at the four corners by using pins. 0.5 g of each of the bleaching-detergent compositions of Examples and Comparative Examples was sprinkled over this cloth, and water was then sprayed thereon. After being allowed to stand for 15 minutes, the cloth was washed with water and then dried with air. After drying, the state of the cloth was evaluated on the basis of the criteria described below for the purpose of measuring the degree of discoloration.

3 marks: The parts in contact with each bleaching-detergent composition were remarkably discolored and many spots were observed.

2 marks: The parts in contact with each bleaching-detergent composition were discolored and spots were clearly observed.

1 marks: The parts in contact with each bleaching-detergent composition were slightly discolored and few spots were observed.

0 marks: The parts in contact with each bleaching-detergent composition were not discolored at all and no spots were observed.

EXAMPLE 1

The bleaching and discoloration tests were performed by using sodium percarbonate as a hydrogen peroxide addition product and each of various 1-chloro-nitrogen-containing heterocyclic compounds as an activator in accordance with the method described above. The total concentration of each activator and hydrogen peroxide produced from sodium percarbonate was $3.7 \times 10^{-2}$ moles/l and the ratio of these compounds was shown in Table 1. The results obtained are shown in Table 1.

TABLE 1

| Sample No. | | Activator | Hydrogen peroxide/activator (molar ratio) | Bleaching ratio (%) | Degree of discoloration ΔE (−) | Hydrolysis constant Kh (−) |
|---|---|---|---|---|---|---|
| Comparative example· | 1 | No activator added | 100/0 | 34 | 1.0 | — |
| Compositions of this invention | 2 | 1-Chloro-4-hydroxy-2,2,6,6-tetramethylpiperidine | 95/5 | 47 | 2.0 | $1.4 \times 10^{-7}$ |
| | 3 | 1-Chloro-4-hydroxy-2,2,6,6-tetramethylpiperidine | 90/10 | 59 | 2.3 | |
| | 4 | 1-Chloro-4-hydroxy-2,2,6,6-tetramethylpiperidine | 80/20 | 66 | 3.5 | |
| | 5 | 1-Chloro-4-hydroxy-2,2,6,6-tetramethylpiperidine | 70/30 | 69 | 4.2 | |
| | 6 | 1-Chloro-4-hydroxy-2,2,6,6-tetramethylpiperidine | 60/40 | 69 | 5.0 | |
| | 7 | 1-Chloro-4-hydroxy-2,2,6,6-tetramethylpiperidine | 50/50 | 69 | 6.0 | |
| | 8 | 1-Chloro-4-hydroxy-2,2,6,6-tetramethylpiperidine | 40/60 | 64 | 6.4 | |
| | 9 | 1-Chloro-4-hydroxy-2,2,6,6-tetramethylpiperidine | 20/80 | 51 | 6.0 | |
| Comparative example | 10 | 1-Chloro-4-hydroxy-2,2,6,6-tetramethylpiperidine | 0/100 | 26 | 5.0 | |
| Compositions of this invention | 11 | 1-Chloro-piperidine | 50/50 | 57 | 2.2 | $1.0 \times 10^{-6}$ |
| | 12 | 1-Chloro-2-methyl-piperidine | 50/50 | 59 | 2.4 | $1.3 \times 10^{-6}$ |
| | 13 | 1-Chloro-3,5-dimethyl-piperidine | 50/50 | 46 | 2.0 | $1.1 \times 10^{-6}$ |
| | 14 | 1-Chloro-isonipecotic acid | 50/50 | 47 | 2.5 | $1.0 \times 10^{-7}$ |
| | 15 | 1-Chloro-hexamethyleneimine | 50/50 | 67 | 6.0 | $1.3 \times 10^{-6}$ |
| | 16 | 1-Chloro-ε-caprolactam | 50/50 | 50 | 6.0 | $5.4 \times 10^{-7}$ |
| Comparative example | 17 | Sodium dichloroisocyanurate | 50/50 | 18 | 0.5 | $3.0 \times 10^{-4}$ |
| | 18 | N-Chloro-succinic acid imide | 50/50 | 27 | 1.5 | $7.0 \times 10^{-6}$ |
| | 19 | N-Chloro-benzotriazole | 50/50 | 23 | 1.5 | $4.6 \times 10^{-4}$ |

TABLE 1-continued

| Sample No. | Activator | Hydrogen peroxide/ activator (molar ratio) | Bleaching ratio (%) | Degree of discoloration ΔE (−) | Hydrolysis constant Kh (−) |
|---|---|---|---|---|---|
| 20 | Tetraacetyl glycoluril | 50/50 | 66 | 20.5 | — |

As seen from Table 1, the agent of the comparative example in which no activator was used (No. 1), the compositions in which organic chlorine compounds having large hydrolysis constants were used as activators (No. 17 to 19), and the composition in which tetraacetyl glycoluril (TAGU) producing peracetic acid was used as an activator (No. 20), the comparative examples (No. 17 to 19) showed little discoloration of the dye, but a low bleaching efficiency, and the comparative example (No. 20) showed the properties opposite to those of the examples (No. 17 to 19). However, the compositions of this invention showed a high bleaching efficiency and little discoloration of the dye.

EXAMPLE 2

A bleaching test was performed in the same manner as that of Example 1 except that each of the 1-chloro-nitrogen-containing heterocyclic compounds shown in Table 2 was used as an activator of the component (B). The results are shown in Table 2.

TABLE 2

| Sample No. | | Activator | Activator/ hydrogen peroxide (molar ratio) | Bleaching ratio (%) | Degree of discoloration ΔE (−) |
|---|---|---|---|---|---|
| Comparative example | 1 | No activator added | 0/100 | 34 | 1.0 |
| Composition of this invention | 2 | 1-Chloro-4-[N-(2-hydroxyethyl)-methylamino]-2,2,6,6-tetramethylpiperidine | 50/50 | 66 | 2 |
| | 3 | 1-Chloro-4-[N-2(2,3-dihydroxy-propyl)-methylamino]-2,2,6,6-tetramethylpiperidine | 50/50 | 65 | 2 |
| | 4 | 1-Chloro-4-[N,N-bis(2-hydroxy-ethyl)amino]-2,2,6,6-tetra-methylpiperidine | 50/50 | 67 | 2 |
| | 5 | 1-Chloro-4-[N-(2,3-dihydroxyo-propyl)-butylamino]-2,2,6,6-tetramethylpiperidine | 50/50 | 50 | 3 |
| | 6 | Trimethyl-(1-chloro-2,2,6,6-tetramethyl-4-piperidyl ammonium paratoluenesulfonate | 50/50 | 67 | 2 |
| | 7 | 1-Chloro-4-methoxy-2,2,6,6-tetramethylpiperidine | 50/50 | 60 | 1 |
| | 8 | Spiro[4,5]-8-chloro-2-hydroxy-methyl-7,7,9,9-tetramethyl-8-aza-1,4-dioxadecane | 50/50 | 60 | 1 |
| | 9 | 1-Chloro-4-[N,N-bis(sodium oxycarbonylmethyl)amino]-2,2,6,6-tetramethylpiperidine | 50/50 | 46 | 1 |
| | 10 | 1-Chloro-4-[N-acetyl-N-methyl-amino]-2,2,6,6-tetramethylpiperidine | 50/50 | 64 | 2 |
| | 11 | 1-Chloro-4-dimethylamino-2,2,6,6-tetramethylpiperidine | 50/50 | 65 | 2 |
| | 12 | Dimethyl-(1-chloro-2,2,6,6-tetramethyl-4-piperidyl) ammonium chloride | 50/50 | 60 | 2 |
| Comparative example | 13 | 1-Chloro-4-[N,N-bis(2-hydroxy-ethyl)amino]2,2,6,6-tetramethylpiperidine | 100/0 | 26 | 5 |

As seen from Table 2, each of the agents (Nos. 2 to 12) in which sodium percarbonate and each activator were used in combination on the basis of the present invention exhibited excellent bleaching efficiency and a low degree of discoloration as compared with composition No. 1 in which no activator was used and composition No. 13 in which only an activator was used.

EXAMPLE 3

A bleaching test was used in the same manner as that of Example 1 except that each of various N-chloro-type organic chlorine compounds was employed. The obtained results are shown in Table 3.

TABLE 3

| Sample No. | | Activator | Activator/ hydrogen peroxide (molar ratio) | Bleaching ratio (%) | Degree of discoloration ΔE (−) |
|---|---|---|---|---|---|
| Comparative example | 1 | No activator added | 0/100 | 34 | 1.0 |
| Composition | 2 | N-Chloro-t-butylamine | 10/90 | 43 | 1.5 |

TABLE 3-continued

| Sample No. | | Activator | Activator/ hydrogen peroxide (molar ratio) | Bleaching ratio (%) | Degree of discoloration ΔE (−) |
|---|---|---|---|---|---|
| of this | 3 | " | 20/80 | 46 | 1.8 |
| invention | 4 | " | 30/70 | 49 | 2.0 |
| | 5 | " | 40/60 | 49 | 2.0 |
| | 6 | " | 50/50 | 48 | 1.4 |
| | 7 | " | 60/40 | 47 | 0.8 |
| | 8 | " | 80/20 | 42 | 1.3 |
| Comparative example | 9 | " | 100/0 | 17 | 1.2 |
| Composition of this invention | 10 | N-Chloro-1,1-domethylpropyl-amine | 50/50 | 46 | 1.5 |
| | 11 | 2-(N-Chloroamino)-2-methyl propanol | 50/50 | 55 | 1.8 |
| | 12 | N-Chloro-t-butylamine | 50/50 | 41 | 1.2 |
| | 13 | N-Chloro-t-butylaminoethane | 50/50 | 59 | 2.2 |
| | 14 | 2-(N-Chloro-t-butylamino)-ethanol | 50/50 | 64 | 2.5 |
| | 15 | 2-(N-Chloro-1,1-dimethyl-propylamino)-ethanol | 50/50 | 60 | 2.0 |
| | 16 | 2-(N-Chloro-t-octylamino)-ethanol | 50/50 | 46 | 1.3 |
| | 17 | 3-(N-Chloro-t-butylamino)-1,2-propanediol | 50/50 | 60 | 1.9 |
| | 18 | 2-(N-Chloro-t-butylamino)-acetic acid | 50/50 | 47 | 1.6 |
| | 19 | 3-(N-Chloro-t-butylamino)-1-propionic acid | 50/50 | 44 | 1.5 |
| | 20 | 2-(N-Chloro-t-butylamino)-methanesulfonic acid | 50/50 | 48 | 1.6 |
| | 21 | N-Chloro-cyclohexylamine | 50/50 | 52 | 2.0 |
| | 22 | N-Chloro-N-Methylcyclohexyl-amine | 50/50 | 60 | 2.4 |
| Comparative | 23 | N-Chloro-n-butylamine | 50/50 | 10 | 1.0 |
| example | 24 | N-Chloro-ethanolamine | 50/50 | 15 | 1.1 |
| | 25 | N-Chloro-di-n-butylamine | 50/50 | 9 | 1.0 |
| | 26 | Tetraacetyl glycoluril | 50/50 | 66 | 20.5 |
| | 27 | 2-(N-Chloro-t-butyl)-benzylamine | 50/50 | 37 | 1.1 |

As seen from Table 3, the compositions of the present invention in which the respective activators were used in combination with sodium percarbonate showed high bleaching efficiency as compared with the Comparative Example (No. 1) in which no activator was used. It was also found that composition No. 9 in which only the activator was used, compositions Nos. 23 to 25 in which amines having no hindered amine structure were used as activators, composition No. 26 in which tetraacetyl glycoluril (TAGU) producing peracetic acid was used as an activator, and composition No. 27 in which an activator with a hypohalogenous acid-producing hydrolysis equilibrium constant of $2.5\times10^{-5}$ was used all showed low bleaching efficiency and a large degree of discoloration, so that good effects could not be obtained. The compositions of the present invention, however, were able to maintain their bleaching efficiency at high levels and showed little discoloration.

The hydrolysis constants of the compounds used in Example 3 are shown in Table 4.

TABLE 4

| | Activator | Hydrolysis equilibrium constant KH (−) |
|---|---|---|
| Compositions of this invention | N-Chloro-t-butylamine | $6\times10^{-7}$ to $1\times10^{-8}$ |
| | N-Chloro-1,1-dimethylpropylamine amine | $4.9\times10^{-6}$ |
| | 2-(N-Chloromino)-2-methyl-propanol | $4\times10^{-7}$ to $1\times10^{-8}$ |
| | N-Chloro-t-butylaminoethane | $3\times10^{-7}$ |
| | 2-(N-Chloro-t-butylamino)-ethanol | $2.5\times10^{-7}$ |
| | 3-(N-Chloro-t-butylamino)-1,2-propanediol | $3\times10^{-7}$ |
| Comparative example | 2-(N-Chloro-t-butyl)-benzylamine | $2.5\times10^{-5}$ |

EXAMPLE 4

Each of the bleaching-detergent compositions of Sample Nos. 1 to 7 shown in Table 6 was formed by the mixing in powder form of the granular detergent of the composition shown in Table 5, sodium perborate monohydrate as a hydrogen peroxide addition product, and each of 1-chloro-nitrogen-containing heterocyclic compounds as an activator, and the bleaching and discoloration tests were performed with respect to these compositions. The obtained results are shown in Table 6.

TABLE 5

| Granular detergent composition | |
|---|---|
| Component | Content (wt %) |
| LAS—NA*1 | 10 |
| AS—Na*2 | 2 |
| AOS—Na*3 | 10 |
| Zeolite (4A type) | 16 |
| Sodium silicate | 10 |

TABLE 5-continued

Granular detergent composition

| Component | Content (wt %) |
|---|---|
| Sodium carbonate | 10 |
| Thinopearl CBS-X*4 | 0.2 |
| Enzyme (alkalase 2.0T)*5 | 0.4 |
| Water | 5 |
| Sodium sulfate | balance |

*1 Sodium linear alkylbenzenesulfonate in which the alkyl has 12 carbon atoms.
*2 Sodium alkylsulfate having 10 to 16 carbon atoms.
*3 Sodium α-olefin sulfonate having 14 to 18 carbon atoms.
*4 A distrylbiphenyl-type fluorescent brightener.
*5 The enzyme was subjected to powder blending after spraying and drying.

TABLE 6

| | | | Composition of this invention | | | | | Comparative example | |
|---|---|---|---|---|---|---|---|---|---|
| | | | Sample No. | | | | | | |
| | | | 1 | 2 | 3 | 4 | 5 | 6 | 7 |
| Content in bleaching-detergent composition (wt %) | Activator | 1-Chloro-4-hydroxy-2,2,6,6-tetramethyl-piperidine | 5 | | | | | | |
| | | 1-Chloro-piperidine | | 5 | | | | | |
| | | 1-Chloro-2-methyl-piperidine | | | 5 | | | | |
| | | 1-Chloro-hexamethylene-imine | | | | 5 | | | |
| | | 1-Chloro-ε-caprolactam | | | | | 5 | | |
| | | Tetraacetyl glycoluril | | | | | | 5 | |
| | Sodium perborate mono-hydrate | | 5 | 5 | 5 | 5 | 5 | 5 | 5 |
| | Granular detergent | | 90 | 90 | 90 | 90 | 90 | 90 | 95 |
| Bleaching ratio (%) | | | 51 | 45 | 46 | 53 | 43 | 48 | 30 |
| Degree of discoloration (marks) | | | 0 | 0 | 0 | 0 | 0 | 3 | 0 |

EXAMPLE 5

The bleaching-detergent compositions were formed in the same manner as that of Example 4 except that the activators shown in Table 7 were used in place of the activators used in Example 4, and the bleaching tests were performed with respect to these compositions. The results are shown in Table 7.

TABLE 7

| | | | Composition of this invention | | | | | | | Comparative example | |
|---|---|---|---|---|---|---|---|---|---|---|---|
| | | | Sample No. | | | | | | | | |
| | | | 1 | 2 | 3 | 4 | 5 | 6 | 7 | 8 | 9 |
| Content in bleaching-detergent composition (wt %) | Activator | N-Chloro-t-butylamine | 5 | | | | | | | | |
| | | 2-(N-Chloroamino)-2-methylpropanol | | 5 | | | | | | | |
| | | 2-(N-Chloro-t-butyl-amino)ethanol | | | 5 | | | | | | |
| | | 2-(N-Chloro-t-octyl-amino)-ethanol | | | | 5 | | | | | |
| | | 2-(N-Chloro-t-butyl-amino)-acetic acid | | | | | 5 | | | | |
| | | 2-(N-Chloro-t-butyl-amino)-propionic acid | | | | | | 5 | | | |
| | | N-Chloro-N-methyl-cyclohexylamine | | | | | | | 5 | | |
| | | Tetraacetyl glycoluril | | | | | | | | 5 | |
| | Sodium perborate monohydrate | | 5 | 5 | 5 | 5 | 5 | 5 | 5 | 5 | 5 |
| | Granular detergent | | 90 | 90 | 90 | 90 | 90 | 90 | 90 | 90 | 95 |
| Bleaching ratio (%) | | | 41 | 45 | 49 | 42 | 43 | 40 | 43 | 48 | 30 |
| Degree of discoloration (marks) | | | 0 | 0 | 0 | 0 | 0 | 0 | 0 | 3 | 0 |

EXAMPLE 6

The granular detergents having the compositions shown in table 8 and 9 were prepared, and 5% each of sodium perborate monohydrate and 1-chloro-4-hydroxy-2,2,6,6-tetramethylpiperidine were added to each detergent to form each bleaching detergent composition. The bleaching and discoloration tests were performed with respect to each agent composition.

TABLE 8

| Component | Content (wt %) |
|---|---|
| LAS—Na | 7.0 |
| Fatty alcohol ethoxylate*1 | 2.5 |
| Sodium soap*2 | 2.5 |
| Sodium tripolyphosphate | 36 |
| Sodium silicate | 6 |
| Ethylenediaminetetraacetate (EDTA) | 0.1 |
| Thinopearl CBS-X | 0.2 |
| Sodium carboxymethyl cellulose | 0.5 |
| Water | 8 |
| Sodium sulfate | balance |

*1 Fatty alcohol ethoxylate, the alcohol having 16 to 18 carbon atoms and EO $\bar{P}$ = 7.
*2 Fatty acid soap sodium salt having 16 to 18 carbon atoms.

TABLE 9

| Component | Content (wt %) |
|---|---|
| LAS—Na | 12 |
| As—Na | 5 |
| AES—Na*1 | 5 |
| Zeolite | 12 |
| Sodium silicate | 15 |

TABLE 9-continued

| Component | Content (wt %) |
|---|---|
| Sodium carbonate | 3 |
| Thinopearl CBS-X | 0.2 |
| Water | 5 |
| Sodium sulfate | balance |

*[1]Sodium alkylether sulfate having 12 to 15 carbon atoms and EO $\bar{P}$ = 3.

When a hydrogen peroxide addition product and an activator of the present invention were added to each of the granular detergent bases shown in Table 8 and 9, excellent performance concerning bleaching and excellent discoloration properties which were similar to that of the composition No. 1 shown in Table 6 were exhibited.

EXAMPLE 7

Bleaching-detergent compositions were formed in the same manner as those of Examples 4 and 6 except that sodium percarbonate was used as hydrogen peroxide addition compound. When the bleaching and discoloration test were performed for the compositions formed, excellent effects were obtainable with respect to each of the activators used.

EXAMPLE 8

A bleaching-detergent composition was prepared in the same manner as that of Example 5 except that sodium percarbonate was used in place of sodium perborate monohydrate and N-chloro-t-butylamine was used as an activator. When the bleaching test was performed for this composition prepared, similar effects to those of No. 1 of Example 5 were obtainable.

What is claimed is:

1. A 1-halopiperidine derivative having the following Formula (I):

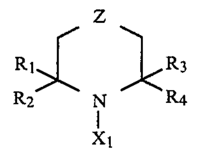

(I)

wherein $R_1$, $R_2$, $R_3$ and $R_4$ each denotes an alkyl group having 1 to 12 carbon atoms and may be the same as or different from each other, $X_1$ denotes a halogen atom; and Z denotes a group having the following formula:

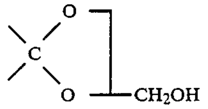

or

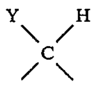

wherein Y denotes an alkoxyl group having 1 to 4 carbon atoms,

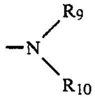

or

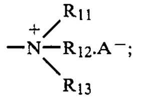

$R_9$ and $R_{10}$ may be the same or different and each denotes $C_mH_{2m+1}$, $C_mH_{2m}OH$, $C_mH_{2m-1}(OH)_2$, $C_mH_{2m}COOM_1$ wherein $M_1$ denotes H or an alkali metal, or an alkanoyl group having 2 to 8 carbon atoms; $R_{11}$ and $R_{12}$ may be the same or different and each denote $C_mH_{2m+1}$, $C_mH_{2m}OH$ or $C_mH_{2m}$-phenyl; $R_{13}$ denotes a hydrogen atom or $C_mH_{2m+1}$; m is an integer from 1 to 4; and $A^-$ denotes an anion selected from the group consisting of $Cl^-$, $CH_3COO^-$, and

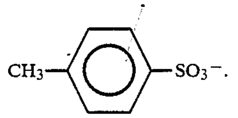

2. A 1-halopiperidine derivative of claim 1 wherein the alkyl group in Formula (I) has 1 to 4 carbon atoms.

* * * * *